(12) United States Patent
Wu et al.

(10) Patent No.: US 6,194,467 B1
(45) Date of Patent: Feb. 27, 2001

(54) DIABETES REMEDIES

(75) Inventors: Hua-Kang Wu; Nobuto Koyama; Eiji Nishiyama; Takanari Tominaga; Michio Hagiya; Ikunoshin Kato, all of Otsu (JP)

(73) Assignee: Takara Shuzo Co., Ltd. (JP)

( * ) Notice: Subject to any disclaimer, the term of this patent is extended or adjusted under 35 U.S.C. 154(b) by 0 days.

(21) Appl. No.: 09/367,163

(22) PCT Filed: Mar. 18, 1998

(86) PCT No.: PCT/JP98/01151

§ 371 Date: Aug. 9, 1999

§ 102(e) Date: Aug. 9, 1999

(87) PCT Pub. No.: WO98/43624

PCT Pub. Date: Oct. 8, 1998

(30) Foreign Application Priority Data

| Mar. 28, 1997 | (JP) | 9-092870 |
| Apr. 15, 1997 | (JP) | 9-111773 |
| Jun. 2, 1997 | (JP) | 9-157324 |
| Jun. 6, 1997 | (JP) | 9-163473 |
| Oct. 1, 1997 | (JP) | 9-283204 |
| Dec. 16, 1997 | (JP) | 9-363281 |

(51) Int. Cl.$^7$ .................................................. A61K 31/12
(52) U.S. Cl. .................................... 514/690; 514/866
(58) Field of Search ........................... 514/690, 866

(56) References Cited

U.S. PATENT DOCUMENTS 5,149,711 * 9/1992 Hazato et al. ................. 514/548
6,087,401 * 7/2000 Koyama et al. ................ 514/690

FOREIGN PATENT DOCUMENTS

| 0 974 347 | 1/2000 | (EP) . |
| 0 978 277 | 2/2000 | (EP) . |
| 0 978 278 | 2/2000 | (EP) . |
| 1 008 345 | 6/2000 | (EP) . |
| 98/13328 * | 4/1998 | (WO) ................. 514/690 |

OTHER PUBLICATIONS

Willson et al, Ann. N. Y. Acad. Sci., vol. 804, pp. 278–283 (abstract), Dec. 1996.*

* cited by examiner

*Primary Examiner*—James H. Reamer
(74) *Attorney, Agent, or Firm*—Kennedy Covington Lobdell & Hickman, LLP (57) ABSTRACT

A therapeutic or preventive agent for diabetes mellitus which is characterized in containing at least one compound selected from a group consisting of 4,5-dihydroxy-2-cyclopenten-1-one represented by the following formula [I] and an optically active substance and a salt thereof as an effective component.

[I]

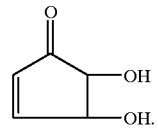

2 Claims, 7 Drawing Sheets

DIABETES REMEDIES

TECHNICAL FIELD OF THE INVENTION

The present invention relates to a drug acting on carbohydrate metabolism and also to food or beverage for improving the symptoms of the diseases caused by abnormality of carbohydrate metabolism or for preventing said diseases.

PRIOR ART

Diabetes mellitus is a compounded disease induced by hyperglycemia and is roughly classified into an insulin-dependent diabetes mellitus where supplement of insulin is required because of deficiency of insulin and a non-insulin dependent diabetes mellitus where the action is not achieved even a sufficient amount of insulin is produced due to the abnormality of receptors or sugar-transporting carrier.

PROBLEMS TO BE SOLVED BY THE INVENTION

An object of the present invention is to develop a compound which normalizes the plasma components and is effective for therapy or prevention of the diseases including diabetes mellitus and to offer drug, food and beverage containing said compound as an effective component.

MEANS TO SOLVE THE PROBLEM

In order to achieve the above-mentioned object, the present inventors have conducted an intensive investigation and found that 4,5-dihydroxy-2-cyclopenten-1-one which is a compound represented by the formula [I] (hereinafter, just referred to as "the cyclopentenone"), an optically active substance or a salt thereof has an inducing ability of differentiation of precursor fat cells such as fibroblast to fat cells and a suppressing ability for production of tumor necrosis factor and is useful for therapy or prevention of diabetes mellitus whereupon the present invention has been accomplished.

Outline of the present invention is that the first feature of the present invention relates to a therapeutic or preventive agent for diabetes mellitus which is characterized in containing at least one compound selected from a group consisting of 4,5-dihydroxy-2-cyclopenten-1-one represented by the following formula [I] and an optically active substance and a salt thereof as an effective component.

[I]

The second feature of the present invention relates to food or beverage for the improvement or prevention of diabetes mellitus which is characterized in containing at least one compound selected from a group consisting of 4,5-dihydroxy-2-cyclopenten-1-one represented by the formula [I] and derivatives and a salt thereof as an effective component.

EMBODIMENTS OF THE INVENTION

The present invention will now be specifically illustrated as hereinafter.

The cyclopentenone represented by the formula [I] used in the present invention covers both isomers where the configurations of hydroxyl groups at 4- and 5-positions are cis and trans. In the present invention, any of cis-cyclopentenone, trans-cyclopentenone and a mixture of cis- and trans-cyclopentenone may be used. It is also possible to use optically active substances thereof.

cis-Cyclopentenone may be prepared by a chemical synthesis [Helvetica Chimica Acta, volume 55, pages 2838–2844 (1972)]. trans-Cyclopentenone may be prepared either by a chemical synthesis [Carbohydrate Res., volume 247, pages 217–222 (1993)] or by heating uronic acid such as glucuronic acid, uronic acid derivative such as glucuronolactone or a substance containing the same (refer to PCT/JP97/03052). In the present invention, it is also possible to use such a heated product or partially purified product or purified product thereof.

For example, when D-glucuronic acid is used as a uronic acid and its 1% solution is heated at 121° C. for four hours, the cyclopentenone is produced in the heat-treated substance. The cyclopentenone in this heat-treated substance is extracted with a solvent and the extract is concentrated. Then, this concentrated extract is separated by means of a silica gel column chromatography, the eluted cyclopentenone fraction is concentrated, the cyclopentenone is extracted with chloroform from the concentrate and the extract of the concentrate is subjected to a normal phase column chromatography whereupon the cyclopentenone in the heat-treated substance is isolated.

Physical property of the cyclopentenone will be given as hereunder. Incidentally, a mass spectrometric analysis of the cyclopentenone was conducted using a mass spectrometer DX302 (manufactured by Nippon Denshi). Further, measurement of an NMR using heavy chloroform as a solvent was conducted by JNM-A 500 (manufactured by Nippon Denshi). Specific rotation was measured by a DIP-370 polarimeter (manufactured by Nippon Bunko) ; ultraviolet absorption spectrum was measured by a UV-2500 spectrophotometer (manufactured by Shimadzu); and infrared absorption spectrum (IR) was measured by an FTIR-8000 infrared spectrophotometer (manufactured by Shimadzu).

MS m/z 115 [M+H]$^+$ $^1$H-NMR (CDCl$_3$): δ 4.20 (1H, d, J=2.4 Hz, 5-H), 4.83 (1H,m, 4-H), 6.30 (1H, dd, J=1.2, 6.1 Hz, 2-H), 7.48 (1H, dd, J=2.1, 6.1 Hz, 3-H).

Incidentally, the chemical shift value of the $^1$H-NMR was given on a basis that the chemical shift value of CHCl$_3$ was 7.26 ppm.

Optical rotation: $[\alpha]_D^{20}$ 0° (c 1.3, water)

UV: $\lambda_{max}$ 215 nm (water)

IR (KBr method): absorptions were noted at 3400, 1715, 1630, 1115, 1060, 1025 cm$^{-1}$.

When the isolated cyclopentenone is subjected to an optical resolution, (−)-4,5-dihydroxy-2-cyclopenten-1-one and (+)-4,5-dihydroxy-2-cyclopenten-1-one are obtained. It goes without saying that the cyclopentenone obtained by a synthetic method can be subjected to an optical resolution as well.

For example, the cyclopentenone is dissolved in ethanol. To this ethanolic solution is further added hexane/ethanol (94/6) to prepare a cyclopentenone solution. The cyclopentenone can be optically resolved when this sample solution is subjected to an HPLC using, for example, a Chiral Pack AS (manufactured by Daicel Chemical Industries) under such a condition that the column temperature was 40° C. and the mobile phase was hexane/ethanol (94/6).

Optical rotation of the optically resolved (−)-trans-4,5-dihydroxy-2-cyclopenten-1-one [hereinafter, referred to as (−)-cyclopentenone] is $[\alpha]_D^{20}$ −105° (c 0.30, ethanol) while that of the optically resolved (+)-trans-4,5-dihydroxy-2-cyclopenten-1-one [hereinafter, referred to as (+)-cyclopentenone] is $[\alpha]_D^{20}$ +104° (c 0.53, ethanol). Incidentally, the optical rotation was measured by the above-mentioned polarimeter of the type DIP-370 (manufactured by Nippon Bunko).

After that, each of (−)-cyclopentenone and (+)-cyclopentenone was subjected to structural analysis by means of mass analysis and nuclear magnetic resonance (NMR), measurement of UV absorption spectrum and measurement of infrared absorption spectrum by the method mentioned already. As a result, both optically active substances showed the same result as that of the cyclopentenone before the optical resolution.

Each of the optically resolved (−)-cyclopentenone and (+)-cyclopentenone was converted to a p-dimethylaminobenzoyl derivative, the circular dichroism spectrum (CD) was measured using a circular dichroism dispersimeter of type J-720 (manufactured by Nippon Bunko) and the result was applied to a dibenzoate chirality rule [J. Am. Chem. Soc., volume 91, pages 3989–3991 (1969)] to determine the configuration.

Figure 6:
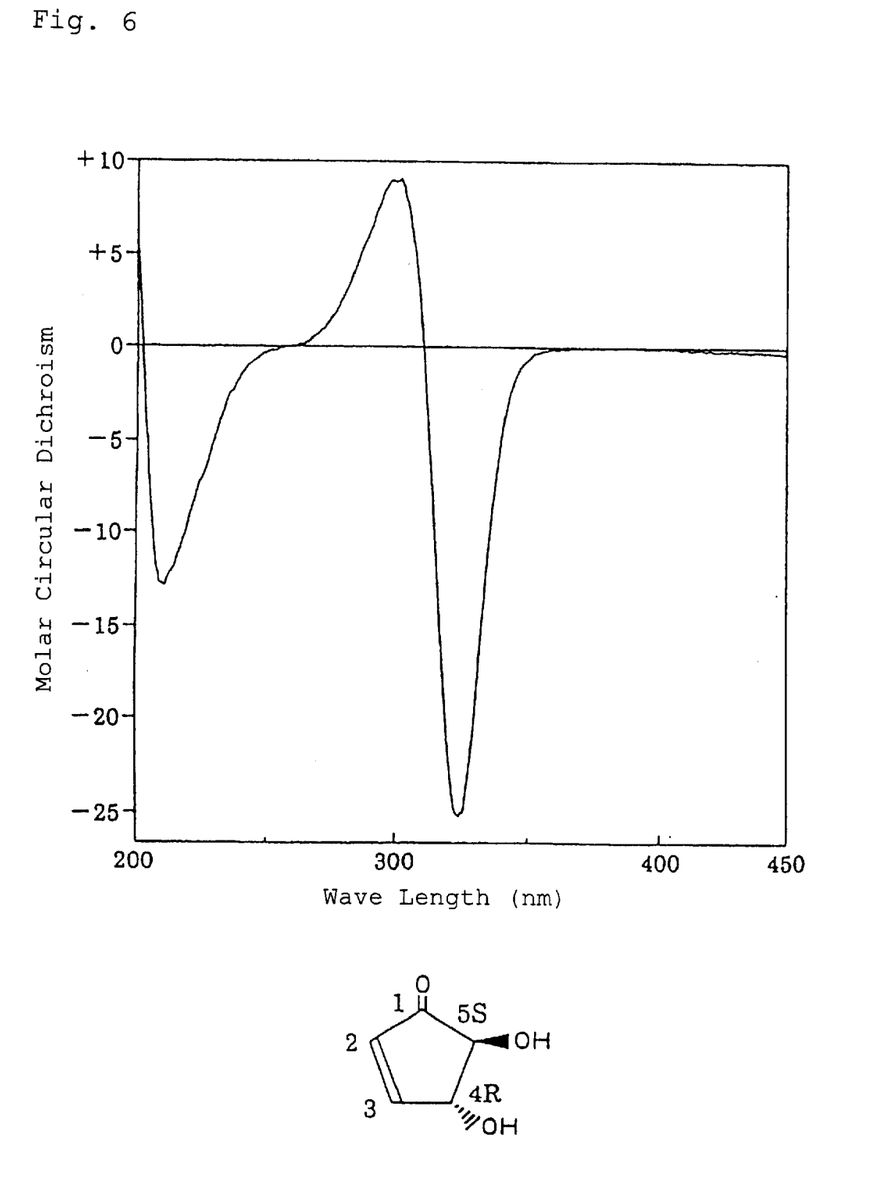
FIG. 6 shows a CD of p-dimethylaminobenzoyl derivative of (−)-cyclopentenone and a stereostructure of (−)-cyclopentenone.

CD of p-dimethylaminobenzoyl derivative of (−)-cyclopentanone and stereostructure of (−)-cyclopentenone are shown in FIG. 6. In the drawing, the ordinate indicates molar circular dichroism while the abscissa indicates wave length (nm). Incidentally, the above stereostructure is given hereunder as the formula [II]

[II]

Figure 7:
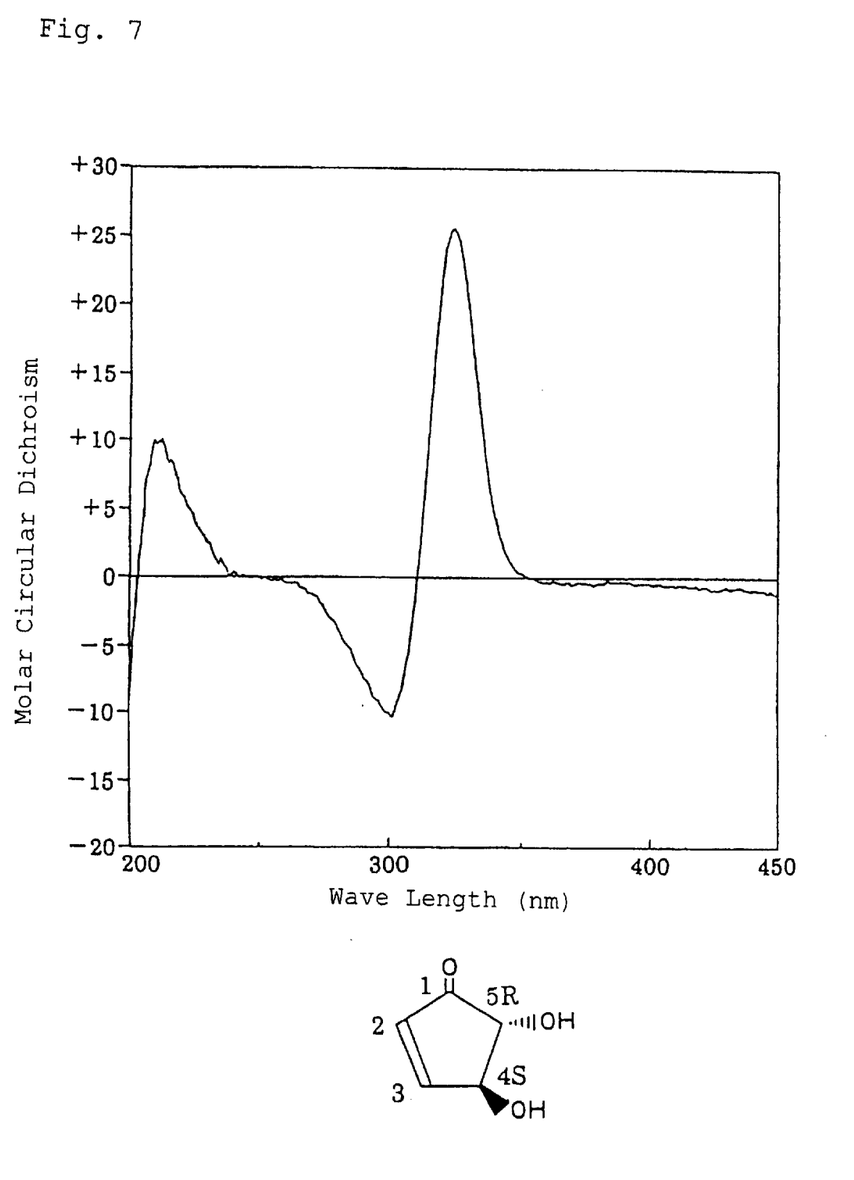
FIG. 7 shows a CD of p-dimethylaminobenzoyl derivative of (+)-cyclopentenone and a stereostructure of (+)-cyclopentenone.

CD of p-dimethylaminobenzoyl derivative of (+)-cyclopentanone and stereostructure of (+)-cyclopentenone are shown in FIG. 7. In the drawing, the ordinate indicates molar circular dichroism while the abscissa indicates wave length (nm). Incidentally, the above stereostructure is given hereunder as the formula [III]

[III]

As shown in FIG. 6, FIG. 7, formula [II] and formula [III], the (−)-cyclopentenone is (−)-(4R,5S)-trans-4,5-dihydroxy-2-cyclopenten-1-one while the (+)-cyclopentenone is (+)-(4S,5R)-trans-4,5-dihydroxy-2-cyclopenten-1-one.

The above-mentioned cyclopentenones or an optically active substance thereof may be manufactured by any method, i.e. they may be manufactured by a method disclosed in this specification or by means of chemical synthesis; and trans- and cis-cyclopentenone or a mixture thereof and an optically active substance thereof may be used in the present invention as well.

Examples of the salt of the cyclopentenone or optically active substance thereof are pharmaceutically acceptable salts and they may be prepared by known converting methods.

The cyclopentenone reacts, for example, with an SH-containing compound (such as cysteine and glutathione) in vivo to produce a metabolic derivative which is useful as a drug. Therefore, it is believed that the pharmaceutical effect of the metabolic derivative is achieved even when the cyclopentenone is administered as well. The reaction product of the cyclopentenone with an SH-containing compound in vivo is presumed to be one of the metabolically effective substances.

Thus, when exemplification is done for an SH-containing compound (R-SH), it reacts with the SH-containing compound to give a compound represented, for example, by the following formula [IV] or [V]. In addition, a compound represented by the formula [V] is converted to a compound represented by the formula [IV].

As such, the cyclopentenone is converted to each of the metabolic derivatives in the presence of an SH-containing compound (R-SH) and such a metabolic derivative produced in vivo achieves an effect as a drug too.

[IV]

(R is a residual group where an SH group is removed from the SH-containing compound.)

[V]

(R is a residual group where an SH group is removed from the SH-containing compound.)

Accordingly, the use of the cyclopentenone, its optically active substance or salt thereof having an object of production of such a reaction product in vivo, i.e. a metabolic derivative, is covered by the present invention as well.

As a result of pathological studies for diabetes mellitus in recent years, it was reported that normal fat cells play an important role in normal systemic insulin action and that, for a smooth progress of saccharide metabolism, normal fat cells are necessary [Jikken Igaku, volume 14, pages 61–68 (1996)].

The cyclopentenone, its optically active substance or salt thereof has an ability of inducing the differentiation of precursor of fat cells such as precursor of fibroblast and induces the differentiation of said cells to fat cells. Therefore, when the cyclopentenone, its optically active substance or salt thereof is administered, normal fat cells increase whereby symptom of diabetes mellitus is assumed to be improved.

The cyclopentenone, its optically active substance or salt thereof has a hypoglycemic activity and it is now possible to prepare a therapeutic or preventive agent for diabetes mellitus containing at least one compound selected from the cyclopentenone, its optically active substance or salt thereof as an effective component.

Thus, when at least one compound selected from the cyclopentenone, its optically active substance or salt thereof is used as an effective component and is made into a pharmaceutical preparation by combining with known pharmaceutical carriers, it is now possible to prepare a therapeutic or preventive agent for diabetes mellitus. Generally, the cyclopentenone, its optically active substance or salt thereof is compounded with a pharmaceutically acceptable liquid or solid carrier and, if necessary, solvent, dispersing agent, emulsifier, buffer, stabilizer, filler, binder, disintegrating agent, lubricant, etc. are added thereto to give said pharmaceutical preparation which may be in solid such as tablets, granules, diluted powders, powders, capsules, etc. or in liquid such as solutions, suspensions, emulsions, etc. Further, this may be in a dry preparation which can be made into liquid by adding an appropriate carrier before use.

The pharmaceutical carrier may be selected depending upon the above-mentioned mode of the administration and form of the preparation. In the case of oral preparations, starch, lactose, sugar, mannitol, carboxymethyl cellulose, corn starch, inorganic salts, etc. may be used. In the manufacture of oral preparations, binders, disintegrating agents, surface-active agents, lubricants, fluidity promoters, taste-correctives, coloring agents, flavors, etc. may be further compounded therewith.

On the other hand, in the case of parenteral preparations, they may be prepared by common methods where the cyclopentenone, its optically active substance or salt thereof which is an effective component of the present invention is dissolved or suspended in a diluent such as distilled water for injection, physiological saline solution, aqueous solution of glucose, vegetable oil for injection, sesame oil, peanut oil, soybean oil, corn oil, propylene glycol, polyethylene glycol, etc. followed, if necessary, by adding bactericides, stabilizers, isotonic agents, analgesics, etc. thereto.

The therapeutic or preventive agent for diabetes mellitus of the present invention is administered by an appropriate route depending upon the form of the preparation. There is no particular limitation for the method of administration as well and it may be administered by means of oral use, external use and injection. Injection preparations are administered, for example, intravenously, intramuscularly, subcutaneously, intracutaneously, etc. while preparations for external use include suppositories, etc.

The dose as the therapeutic or preventive agent for diabetes mellitus is not particularly specified but may be appropriately determined depending upon the dosage form, administration method, purpose of the use and age, body weight, conditions, etc. of the patient. Usually, however, the amount of at least one of the compound selected from the cyclopentenone, its optically active substance or salt thereof contained in the preparation for an adult is 10 pg-200 mg/kg per day. As a matter of course, the dose may vary depending upon various factors and, therefore, the dose less than the above-mentioned one may be sufficient in some cases while, in other cases, the dose more than the above may be necessary. The agent of the present invention may be administered orally as it is and, further, the agent may be taken daily after adding to common food and/or beverage as well.

Further, the cyclopentenone, its optically active substance or salt thereof may be used as a material for the food or beverage for the improvement or prevention of diabetes mellitus. When a product containing the cyclopentenone, its optically active substance or salt thereof is taken, diabetes mellitus is improved and the amount of sugar in urine significantly decreases. In addition, complications such as hypogonadism is markedly improved. Further, hyperlipemia is improved as well.

The cyclopentenone, its optically active substance or salt thereof has an activity of improving the hyperlipemia or activity of reducing the total cholesterol in serum, activity of reducing the triglycerides in serum and activity of reducing the free fatty acids in serum and, when at least one compound selected from the cyclopentenone, its optically active substance or salt thereof having such an activity is used as an effective component and is made into pharmaceutical preparation by combining with known pharmaceutical carriers, it is now possible to manufacture an agent for therapy or prevention of hyperlipemia. Manufacture of such a preparation can be conducted by the same manner as in the case of the above-mentioned therapeutic or preventive agent for diabetes mellitus and such a preparation can be administered by the same manner as in said therapeutic or preventive agent for diabetes mellitus. In addition, the cyclopentenone, its optically active substance or salt thereof may be used as a material for food or beverage for improvement or prevention of hyperlipemia. When the product containing the cyclopentenone, its optically active substance or salt thereof is taken, hyperlipemia is improved and lipid level in blood is significantly reduced.

In addition, when the cyclopentenone, its optically active substance or salt thereof having an ability of inducing the differentiation of the fat cell precursor to fat cells is used as an effective component and made into pharmaceutical preparations combining with the known pharmaceutical carriers, it is now possible to manufacture an agent for inducing the differentiation of precursor fat cells to fat cells. Manufacture of said agent may be conducted by the same manner as in the case of above-mentioned therapeutic or preventive agent for diabetes mellitus and the agent may be administered by the same manner as in the case of the therapeutic or preventive agent for diabetes mellitus.

Further, the cyclopentenone, its optically active substance or salt thereof has an inhibition activity of the production of tumor necrosis factor and is useful for therapy or prevention of non insulin dependent diabetes mellitus caused by tumor necrosis factor [Nature, volume 389, pages 610–614 (1997)].

A drug containing at least one compound selected from the cyclopentenone, its optically active substance and salt thereof is useful as an agent for inducing a differentiation of fat cell precursor to fat cells and as an agent for inhibiting the tumor necrosis factor production. When the cyclopentenone, its optically active substance or salt thereof is administered, improvement in blood sugar level and normalization of insulin value are noted and the drug of the present invention can be used as a therapeutic agent or a preventive agent for diabetes mellitus. In addition, administration of a drug of the present invention normalizes the triglyceride and free fatty acid levels in plasma and the drug of the present invention can be used as a drug for therapy or prevention of hyperlipemia.

Further, an agent for inducing the differentiation of fat cell precursor to fat cells containing the cyclopentenone, its optically active substance or salt thereof is a differentiation inducing agent useful in biochemical research, etc. and, when said differentiation inducing agent is used, a method for inducing the differentiation of fat cell precursor to fat cell which is useful in the biochemical research, etc. can be offered and, when said method is used, it is possible to screen the inhibitors for differentiation induction and the differentiation inducing agents.

In the present invention, a material selected from the cyclopentenone, its optically active substance or salt thereof, a heat-treated substance containing the cyclopentenone and a partially purified cyclopentenone from said heat-treated substance is used for offering food or beverage for improvement or prevention of diabetes mellitus, food or beverage for improvement or prevention of hyperlipemia and food or beverage for inducing the differentiation of fat cell precursor to fat cell.

Thus, food or beverage which manufactured by diluting and/or adding a material selected from the cyclopentenone-containing heat treated product, partially purified cyclopentenone and purified cyclopentenone from the heat treated product, or the cyclopentenone, an optically active substance thereof or a salt thereof is covered by food or beverage of the present invention.

There is no particular limitation for the method of manufacturing food or beverage of the present invention but cooking, processing and commonly-used manufacturing methods for food or beverage may be applied provided that at least one compound selected from the cyclopentenone, an optically active substance or a salt thereof having an improving or preventing action for diabetes mellitus is contained in the resulting food or beverage as an effective component.

There is no particular limitation for the shape of food or beverage of the present invention so far as at least one compound selected from the cyclopentenone, an optically active substance or a salt thereof having an improving or preventing action for diabetes mellitus is contained therein, added thereto and/or diluted therein. Thus, the shape includes the ones which can be orally taken such as tablets, granules, capsules, gel and sol.

Furthermore, no toxicity was observed in the compound used in the present invention even when the dose which is effective to achieve those physiological activities is administered. In the case of oral administration for example, no dead case was observed in rats by a single oral administration of 100 mg/kg of any of the cyclopentenone, an optically active substance or a salt thereof.

EXAMPLES

The present invention will be further illustrated by way of the following examples although the present invention is never limited to those examples. Incidentally, "%" used in the examples stands for "% by weight".

Referential Example 1

D-Glucuroic acid (G 5269; manufactured by Sigma) (10 g) was dissolved in 1 liter of water, heated at 121° C. for four hours and concentrated in vacuo until about 10 ml. This was mixed with 40 ml of an upper layer of a 3:2:2 mixture of butyl acetate, acetic acid and water and centrifuged and the resulting supernatant liquid was concentrated in vacuo until about 10 ml.

The above extract was applied to silica gel (BW-300SP; 2×28 cm; manufactured by Fuji Silycia) for a column chromatography and separated using an upper layer of a 3:2:2 mixture of butyl acetate, acetic acid and water as an eluate at the flow rate of about 5 ml/minute under a pressure of 0.2 kg/cm$^2$ using a compressor. Fractionation was conducted to make a volume of one fraction 10 ml and a part of each fraction was analyzed by a thin layer chromatography whereupon cyclopentenone of a high purity was contained in 61st to 80th fractions. Those fractions were collected, concentrated in vacuo, extracted with 40 ml of chloroform and the extract was concentrated in vacuo to afford 100 mg of cyclopentenone.

The fraction was separated by means of a normal phase HPLC using a Palpack type S column (manufactured by Takara Shuzo) and, when a detection was conducted by an ultraviolet absorption of 215 nm, the purity was found to be 98%.

The above cyclopentenone (113.9 mg) was dissolved in 2.85 ml of ethanol. To this ethanolic solution was added 3.85 ml of hexane/ethanol (94/6) to prepare a cyclopentenone solution (17 mg/ml). This solution was filtered through a filter of 0.5 μm to prepare a sample solution for an optical resolution HPLC.

This sample solution was applied to an optical resolution HPLC, each of the fractions of the (−)-cyclopentenone in the earlier peak and the (+)-cyclopentenone in the later peak was collected and evaporated to dryness in vacuo to give 43.2 mg of the (−)-cyclopentenone and 43.0 mg of the (+)-cyclopentenone.

Conditions for Optical Resolution HPLC

Columns: Chiral Pack AS (manufactured by Daicel) 2.0 cm×25.0 cm

Column temperature: 40° C.

Mobile phase: hexane/ethanol (94/6)

Flow rate: 14.0 ml/minute

Detection: UV 210 nm

Amount of the charged sample: 150 μl (2.55 mg)

Each of the (−)-cyclopentenone and (+)-cyclopentenone obtained herein contains about 1% of enantiomer and, therefore, they were subjected to an optical resolution under the above-mentioned conditions again. As a result, 19.7 mg of the (−)-cyclopentenone containing no enantiomer was obtained from 30.0 mg of the (−)-cyclopentenone of the earlier peak while, from 37.4 mg of the (+)-cyclopentenone of the later peak, 27.7 mg of the (+)-cyclopentenone containing no enantiomer was obtained. Incidentally, the eluting times in optical resolution HPLC of the (−)-cyclopentenone and (+)-cyclopentenone were 33 minutes and 40 minutes, respectively.

Example 1

3T3-L1 cells (ATCC CL-173) which were the fibroblast precursor cells derived from fetus of mouse were incubated in a Dulbecco-modified Eagle's medium (DMEM) containing 5% of fetal calf serum (FCS) until a 90% confluence was resulted. In the meanwhile, the cyclopentenone prepared by a method mentioned in Referential Example 1 in a concentration of $10^{-1}$, $10^{-2}$, $10^{-3}$, $10^{-4}$, $10^{-5}$, $10^{-6}$, $10^{-7}$, $10^{-8}$ or $10^{-9}$ μg/ml or insulin (available from Takara Shuzo) in a concentration of 100, 50, 10, 5, 1 or 0.2 μg/ml was added to a DMEM containing 5% of the high-molecular fraction obtained by ultrafiltration of FCS using an ultrafilter having a fractionating molecular weight of 30,000 followed by subjecting to a treatment with proteinase K, pronase and leucine aminopeptidase (hereinafter, referred to as enzyme-treated FCS) and then incubation was conducted for nine days. Incidentally, after three days and six days during the incubation, an exchange was conducted with a fresh medium containing the cyclopentenone or insulin of each concentration. The fat contained in the medium cells was stained with Oil Red O (manufactured by Sigma) and observed under a microscope. When the cells were differentiated to fat cells and fat is accumulated, staining in red color is noted.

The result is shown in Table 1. In Table 1, − means that no accumulation of fat was noted; ± means that accumulation of fat was noted in less than 25% of the cells; + means that accumulation of fat was noted in from 25% to less than 50% of the cells; ++ means that accumulation of fat was noted in from 50% to less than 75% of the cells; and +++ means that accumulation of fat was noted in 75% or more of the cells.

TABLE 1

| | Degree of Accumulation of Fat |
|---|---|
| Cyclopentenone (μg/ml) | |
| $10^{-1}$ | ± |
| $10^{-2}$ | + |
| $10^{-3}$ | ++ |
| $10^{-4}$ | ++ |
| $10^{-5}$ | +++ |
| $10^{-6}$ | +++ |
| $10^{-7}$ | ++ |
| $10^{-8}$ | ± |
| $10^{-9}$ | − |
| 0 | − |
| Insulin (μg/ml) | |
| 100 | ++ |
| 50 | +++ |
| 10 | +++ |
| 5 | ++ |
| 1 | + |
| 0.2 | + |
| 0 | − |

As shown in Table 1, degree of accumulation of fat was +++ when 10–50 μg/ml of insulin was added while, when $10^{-5}$~$10^{-6}$ μg/ml of the cyclopentenone was added, degree of accumulation of fat was +++. The cyclopentenone showed an activity of differentiation induction to fat cells in low concentrations.

(−)-Cyclopentenone and (+)-cyclopentenone showed the same results as well.

Example 2

(1) KK-A$^y$ mice (male; ten weeks age; body weight about 40 g) which were the mice where non-insulin dependent diabetes mellitus naturally occurred were purchased from Clea Japan. CE-2 (Clea Japan) was given as a feed and, after a single preliminary feeding, the mice of 11 weeks age were subjected to the test. Mice (8~9 per group) were compulsorily administered per os with 0.1 mg, 1 mg or 10 mg/kg of the cyclopentenone prepared by a method mentioned in Referential Example 1 once daily until the fourth day (for five times in total) and, on the fourth day, blood was collected from vein of eyeground. Water instead of the cyclopentenone was administered to a control group and blood was collected by the same manner. After separation of plasma, amount of glucose in the plasma was measured by a reagent for glucose determination (GLU Neo Shinotest; Shinotest).

The result is given in Table 2. In the cyclopentenone-administered group, the blood sugar level in plasma was reduced on a dose-dependent manner as compared with the control group and, especially in the case of the group administered with 10 mg/kg/day for five times, the blood sugar level in plasma were reduced as compared with that of the control group. Incidentally, there was no difference in terms of gain or loss of body weight between the cyclopentenone-administered group and the control group.

TABLE 2

| Dose of Cyclopentenone (mg/kg/day) | Numbers of Mice | Glucose in Plasma (mg/dl) (in the Blood Collected on 4th Day) |
|---|---|---|
| — (control) | 9 | 432.3 ± 45.4 |
| 0.1 | 8 | 411.9 ± 44.0 |
| 1 | 9 | 327.9 ± 25.4 |
| 10 | 9 | 269.8 ± 28.5 |

Figure 1:
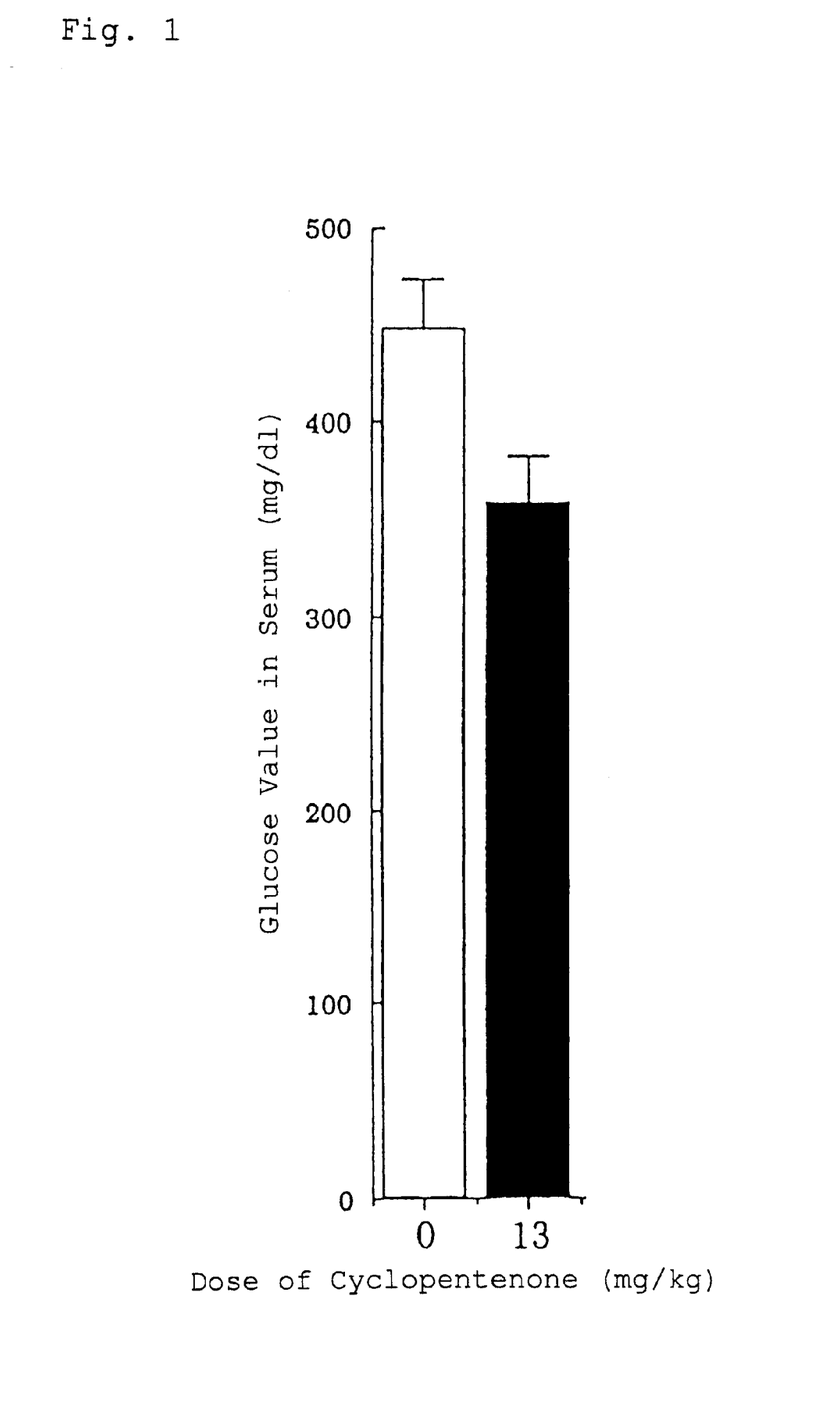
FIG. 1 shows a relation between the dose of cyclopentenone and blood sugar level.
Figure 2:
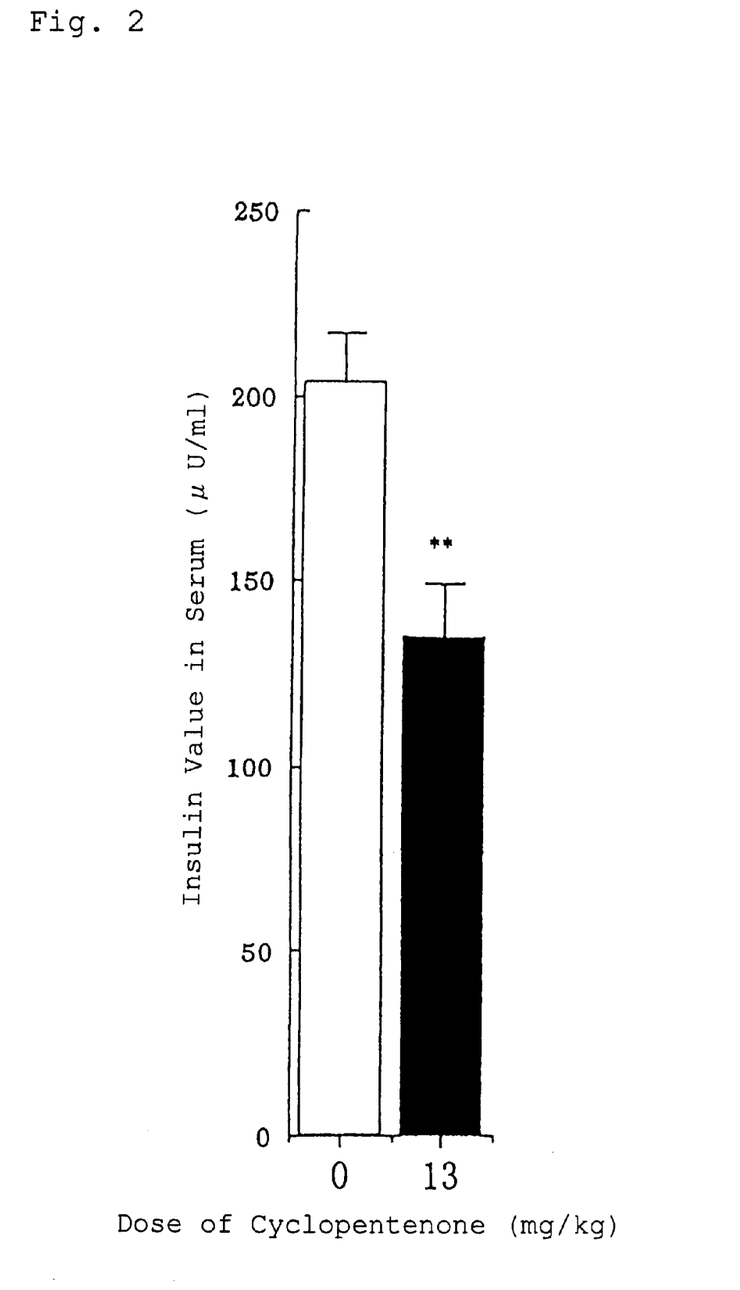
FIG. 2 shows a relation between the dose of cyclopentenone and the insulin level in serum.
Figure 3:
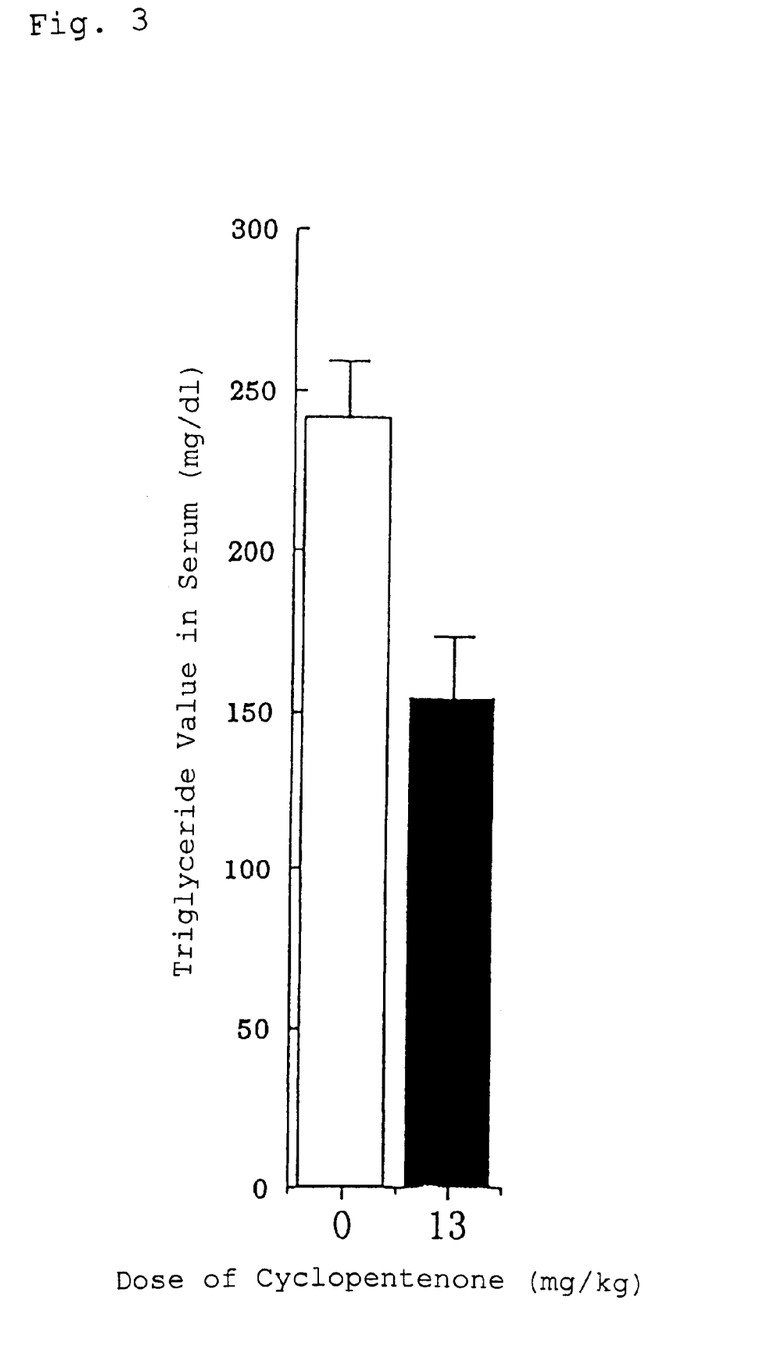
FIG. 3 shows the relation between the dose of cyclopentenone and the triglyceride level in serum.
Figure 4:
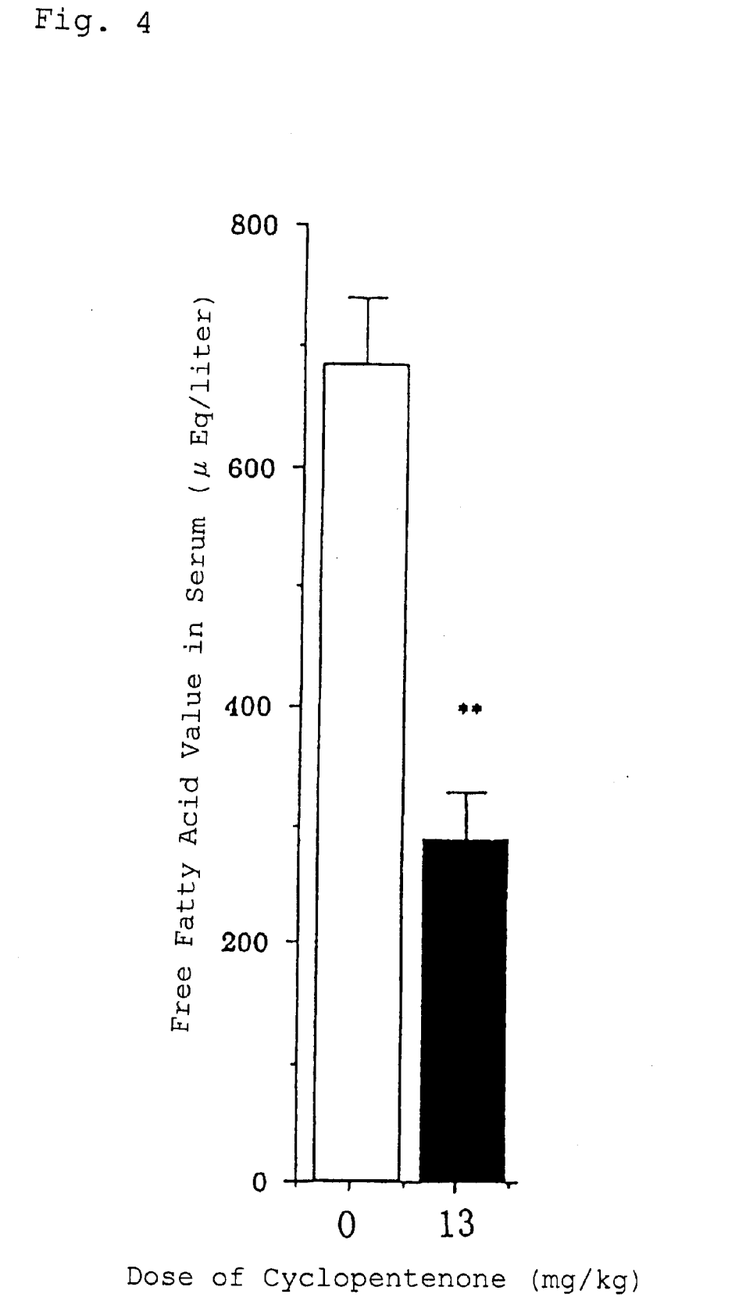
FIG. 4 shows the relation between the dose of cyclopentenone and the free fatty acid level in serum.

(2) KK-A$^y$ Mice (male; four weeks age) were purchased from Clea Japan and, after breeding at our end until ten weeks age, the cyclopentenone prepared by a method mentioned in Referential Example 1 was orally administered for 14 days and its influence on sugar, insulin and lipid in blood was investigated. Doses of cyclopentenone were 13 mg/kg. Blood sugar decreased in each of the groups administered with 13 mg/kg of cyclopentenone (FIG. 1). Insulin in serum decreased in each of the groups administered with 13 mg/kg of cyclopentenone (FIG. 2). With regard to lipid in serum, triglycerides in serum decreased in the 13 mg/kg of cyclopentenone-administered group (FIG. 3) and free fatty acids in serum decreased in the 13 mg/kg of cyclopentenone-administered group (FIG. 4).

Thus, FIG. 1 shows the relation between the dose of cyclopentenone and blood sugar in which ordinate indicates glucose value in serum (mg/dl) while abscissa indicates dose of cyclopentenone (mg/kg). FIG. 2 shows the relation between the dose of cyclopentenone and insulin in serum in which ordinate indicates insulin value in serum (μU/ml) while abscissa indicates dose of cyclopentenone (mg/kg). FIG. 3 shows the relation between the dose of cyclopentenone and triglyceride value in serum in which ordinate indicates triglyceride value in serum (mg/dl) while abscissa indicates dose of cyclopentenone (mg/kg). FIG. 4 shows the relation between the dose of cyclopentenone and free fatty acid value in serum in which ordinate indicates free fatty acid value in serum (μEq/liter) while abscissa indicates dose of cyclopentenone (mg/kg). In the drawings, * and ** mean that significances in a Turkey's multiple comparative test to the group to which no cyclopentenone was administered were p<0.05 and p<0.01, respectively.

Incidentally, the animals were grouped into two (each group consisting of ten animals) and the two groups were administered with physiological saline solution (5 ml/kg) or 13 mg/5 ml/kg of cyclopentenone. Each test substance was orally administered once daily for 14 days and, on the final day of administration, the animals were anesthetized with ether after four hours from the administration of the test substance and blood was collected from artery of lower abdomen.

Insulin in serum was measured by an enzyme-immunoassay (commercially available kit: Glazym Insulin-EIATEST, manufactured by Wako Pure Chemicals). Sugar, triglycerides and free fatty acids in serum were measured using an automatic analyzer (type 7070, manufactured by Hitachi) by a hexonase-G6PDH method, a GPO·DAOS method and an ACS·ACOD method, respectively.

From the above results, cyclopentenone was found to have an effect of lowering blood sugar, insulin and lipid.

(−)-Cyclopentenone and (+)-cyclopentenone showed the same results as well.

Example 3

(1) LPS (lipopolysaccharide; manufactured by Sigma) derived from *Salmonella abortus* equi dissolved in a physiological saline solution was intraperitoneally administered (0.1 mg/kg) to female mice of CDF1 strain of 20 weeks age to prepare endotoxin-shock models.

The cyclopentenone was administered either intraperitoneally or orally at a dose of 30 mg/kg at 30 minutes before the administration of LPS. On the other hand, the control group was not administered as such. After 90 minutes from the administration of LPS, blood was collected from the mice and serum was separated. Then the amount of tumor necrosis factor in the serum was measured by means of a TNF-α·ELISA Kit (manufactured by Genzyme) and the effect of inhibiting the tumor necrosis factor production by administration of the cyclopentenone was measured.

The result is given in Table 3. Thus, as compared with the control group, concentrations of tumor necrosis factor in the serum were low in the cyclopentenone-administered groups both in the groups of intraperitoneal and oral administrations whereby production of tumor necrosis factor was significantly suppressed by administration of the cyclopentenone.

TABLE 3

| Groups | Numbers of Mice | TNF-α in Serum (ng/ml) Average ± SE |
|---|---|---|
| Control group | 5 | 3.96 ± 0.52 |
| Cyclopentenone-administered group (intraperitoneal administration) | 5 | 0.58 ± 0.08** |
| Cyclopentenone-administered group (oral administration) | 5 | 1.80 ± 0.30* |

**: having significant difference to control at $p < 0.001$
*: having significant difference to control at $p < 0.01$ (2) LPS was intraperitoneally injected (10 μg/mouse) to female CDF1 mice of eight weeks age and endotoxin-shock models were prepared. The cyclopentenone was subcutaneously administered at the dose of 0.03, 0.3, 3 and 30 mg/kg at fifteen minutes before administration of LPS (each group consisting of four mice). After one hour from the administration of LPS, blood was collected from the mice, serum was separated and amount of the tumor necrosis factor-α in the serum was measured by a commercially available ELISA kit (manufactured by Endogen). The result is shown in Table 4. Thus, the cyclopentenone suppressed an increase in the concentration of tumor necrosis factor-α in serum by administration of LPS on a dose-dependent manner.

TABLE 4

| | Dose (mg/kg) | Tumor Necrosis Factor (ng/ml) Average ± SD |
|---|---|---|
| Control group | — | 3.00 ± 0.30 |
| Cyclopentenone-administered group | 30 | 0.24 ± 0.08 |
| | 3 | 1.41 ± 0.45 |
| | 0.3 | 2.30 ± 0.24 |
| | 0.03 | 2.68 ± 0.28 |

(3) Paraffin oil (Cosmo Bio) (2 ml) was intraperitoneally administered to female CDF1 mice of eight weeks age to induce celiac macrophage (Mφ). After one week from administration of paraffin oil, 4 ml of an RPMI-1640 medium (Gibco) was intraperitoneally infused, well massaged and recovered to give celiac cells.

The celiac cells were washed with an RPMI-1640 medium twice and suspended in an RPMI1640 medium containing 10% of fetal calf serum (FCS; High-Clone) to adjust the cell concentration to $1 \times 10^6$ cells/ml. The cell solution (1 ml) prepared as such was planted on a 24-well plate and incubated in a $CO_2$ incubator at 37° C. for two hours. Non-adhesion cells contained in the supernatant liquid after incubation was removed and the adhesion cells were used as celiac Mφ.

To each of the well of the plate was added 800 μl of RPMI-1640 medium containing 10% of FCS, then 100 μl of 1, 10, 100 and 1000 μM cyclopentenone dissolved in a physiological saline solution (manufactured by Otsuka Pharmaceutical) was added thereto and incubation was conducted in a $CO_2$ incubator at 37° C. for one hour.

After the incubation, 100 μl of 100 ng/ml lipopolysaccharide (manufactured by Sigma) was added and incubation was conducted for 24 hours more. After completion of the incubation, the supernatant liquid was recovered therefrom and the amount of TNF-α produced therein was determined using a commercially available ELISA kit (manufactured by Endogen).

Figure 5:
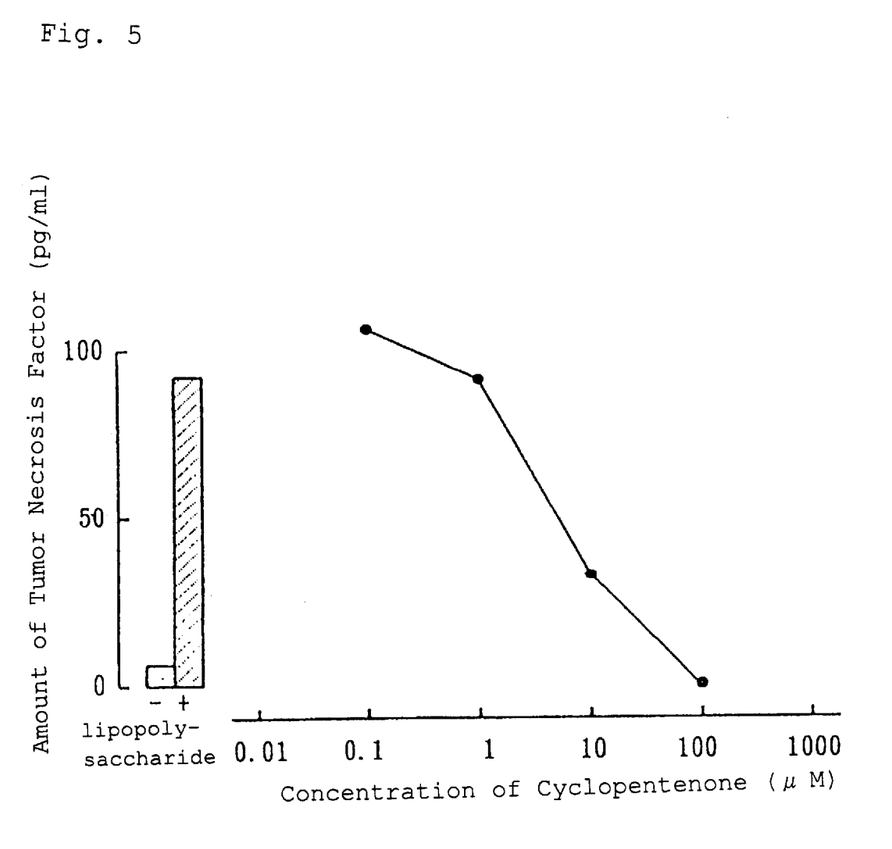
FIG. 5 shows a relation between the quantity of cyclopentenone and the amount of production of tumor necrosis factor.

The result is shown in FIG. 5. Thus, FIG. 5 shows the relation between the concentration of cyclopentenone and the produced amount of tumor necrosis factor in which ordinate indicates amount of tumor necrosis factor (pg/ml) while abscissa indicates concentration of cyclopentenone (μM) of each sample.

The cyclopentenone in a concentration of not less than 10 μM significantly inhibited the production of tumor necrosis factor from celiac macrophage of mice induced by lipopolysaccharide.

As shown in the above, cyclopentenone has an inhibition activity of the production of tumor necrosis factor. (−)-Cyclopentenone and (+)-cyclopentenone showed the same results as well.

Example 4

When 50 ml (containing 2 mg of the cyclopentenone) of the beverage prepared in Example 7-(2) was given every day for three months to a male patient (55 years old) who was diagnosed five years ago as non-insulin dependent diabetes mellitus and treated as a diabetes mellitus by administration of one tablet per day of Euglucon (manufactured by Yamanouchi) but did not show improvement in diabetes mellitus (urinary sugar being +++ when hungry as being measured by a urinary sugar test paper manufactured by Miles-Sankyo), the urinary sugar measured when hungry now became (−) whereupon a significant recovery from non-insulin dependent diabetes mellitus was noted. In addition, together with the recovery from non-insulin dependent diabetes mellitus, significant recovery in sexual function was noted as well.

Example 5
Injection Preparations
(1) Cyclopentenone was added to a physiological saline solution (as listed in the Japanese Pharmacopoeia) in a concentration of 1% to prepare an injection preparation.
(2) (−)-Cyclopentenone and glycyrrhizic acid were added to a physiological saline solution (the same as above) in concentrations of 0.5% and 0.1%, respectively, to prepare an injection preparation.

Example 6
Tablets
(1) A tablet containing 100 mg of cyclopentenone and an appropriate amount of microcrystalline cellulose was prepared and coated with sugar to manufacture a tablet preparation.
(2) A tablet containing 0.1 mg of (+)-cyclopentenone, 10 mg of dipotassium glycyrrhizinate and an appropriate amount of microcrystalline cellulose was prepared and coated with sugar to manufacture a tablet preparation.

Example 7

(1) Pectin (Pomosin Pectin LM-13CG; manufactured by Hercules) (5 kg) was added to 100 liters of tap water and the mixture was heated from the liquid temperature of 28° C. to 120° C. by means of blowing steam thereinto during 35 minutes, kept at 120° C. for five hours with stirring and cooled to prepare 135 liters of cooled mixture. To this were added 1.35 kg of Celite #545 (manufactured by Celite) and 1.35 kg of Silica #600-S (manufactured by Chuo Silica) as filter aids and filtration was conducted using a compact filter (6-inch filter paper in 16 stages; ADVANTEC #327) precoated with 0.1 kg of Celite #545 and 0.1 kg of Silica #600-S. The resulting filtrate was subjected to a continuous instant heating treatment (at 98 ° C. for 60 seconds) using a plate heater (manufactured by Nichihan Seisakusho) followed by cooling to prepare 150 liters of heat-treated pectin solution containing the cyclopentenone.

Said heat-treated pectin solution containing the cyclopentenone had pH of about 3.5, acidity of 6.2 ml and sugar degree of 5.8 Brix %. Incidentally, pH was measured by a pH meter, acidity was expressed in terms of the amount (ml) of 0.1N NaOH used for neutralizing to pH 7.0 and sugar degree was measured by a Brix saccharometer.

(2) Beverage was prepared according to the following formulation.

| | |
|---|---|
| Fructose-Glucose-Liquid Sugar | 5.00% |
| Sugar | 4.00% |
| Acidic agent | 1.20% |
| Perfumes | 0.30% |
| Cyclopentenone-containing material | 0.5% |
| Pure water | balance |
| Total | 100.00% |

The heat-treated pectin solution containing the cyclopentenone mentioned in Example 7-(1) was used as the cyclopentenone-containing material and its amount calculated on a solid basis was added. This beverage (100 ml) contains 4 mg of the cyclopentenone.

MERIT OF THE INVENTION

In accordance with the present invention, a drug having an action of inducing the differentiation of fat cell precursor to fat cell and an action of suppressing the tumor necrosis factor production and having a therapeutic, improving or preventing action for diabetes mellitus, particularly non-insulin dependent diabetes mellitus, is offered. In addition, a drug which is useful for therapy and prevention of hyperlipemia is offered as well.

Further in accordance with the present invention, it is now possible that an appropriate amount of the cyclopentenone or optically active substance or salt thereof having a physiological activity is contained in food or beverage. Because of the action of inducing the differentiation of fat cell precursor to fat cell and the action of suppressing the tumor necrosis factor production of those compounds, the food or beverage of the present invention is useful for improvement or prevention of diabetes mellitus, particularly of non-insulin dependent diabetes mellitus, and for improvement or prevention of symptoms of hyperlipemia and, in addition, it is quite useful for improvement and prevention of symptoms of complications accompanied by diabetes mellitus such as glaucoma, a reduction in sexual function, hyperlipemia, etc.

What is claimed is:

1. A therapeutic or preventive agent for diabetes mellitus which is characterized in containing at least one compound selected from a group consisting of 4,5-dihydroxy-2-cyclopenten-1-one represented by the following formula [I] and an optically active substance and a salt thereof as an effective component

[I]

2. Food or beverage for the improvement or prevention of diabetes mellitus which is characterized in containing at least one compound selected from a group consisting of 4,5-dihydroxy-2-cyclopenten-1-one represented by the following formula [I] and an optically active substance and a salt thereof

[I]

* * * * *